United States Patent [19]

Edwards, II

[11] Patent Number: 4,493,314
[45] Date of Patent: Jan. 15, 1985

[54] HEART PUMP

[75] Inventor: Clifton V. Edwards, II, Essex, Conn.

[73] Assignee: Lundell Laboratories, Inc., Scottsdale, Ariz.

[21] Appl. No.: 393,765

[22] Filed: Jun. 30, 1982

[51] Int. Cl.³ .............................................. A61F 1/24
[52] U.S. Cl. ...................................... 128/1 D; 3/1.7; 417/394
[58] Field of Search ............ 128/1 D; 3/1.7, DIG. 2; 417/394, 395, 321

[56] References Cited

U.S. PATENT DOCUMENTS

| | | | |
|---|---|---|---|
| 3,046,903 | 7/1962 | Jones | 128/1 D |
| 3,379,191 | 4/1968 | Harvey | 128/1 D X |
| 3,411,448 | 11/1968 | Von Wrangell et al. | 128/1 D |
| 3,518,033 | 6/1970 | Anderson | 417/478 |
| 3,568,214 | 3/1971 | Goldschmied | 3/1.7 |
| 3,878,567 | 4/1975 | Purdy | 3/1.7 |
| 4,004,299 | 1/1977 | Runge | 3/1.7 |
| 4,058,855 | 11/1977 | Runge | 3/1.7 |

Primary Examiner—Edward M. Coven
Attorney, Agent, or Firm—Richard R. Mybeck

[57] ABSTRACT

A pulsatible outflow, continuous and non-sucking inflow, artificial heart pump utilizes a pump body in which the ends of a pair of passages open at two spaced locations on the body. One of the passages permits only outflow, and the other permits only inflow; the commonly located ends thereof communicate with one another through passively distensible sacs. Discharge of the sacs is achieved with reciprocating pistons, the stroke and timing of which are controlled by a motor-driven cam ring disposed about the pistons and the pump body.

18 Claims, 9 Drawing Figures

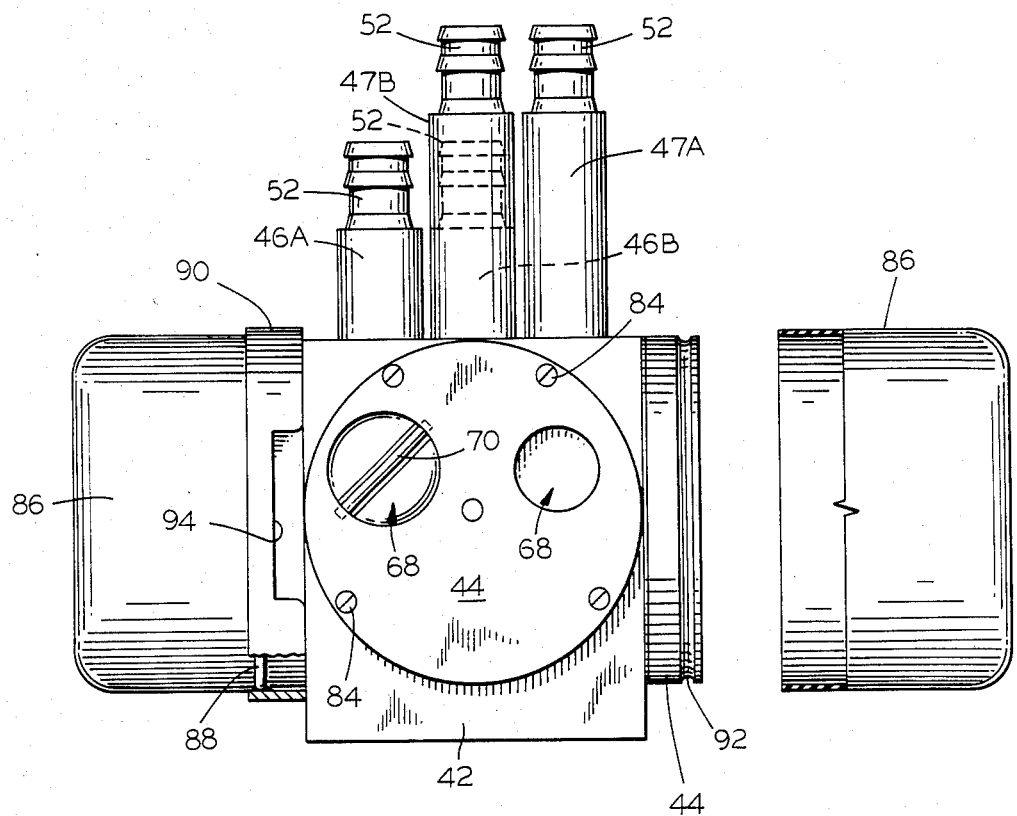
FIG. 3
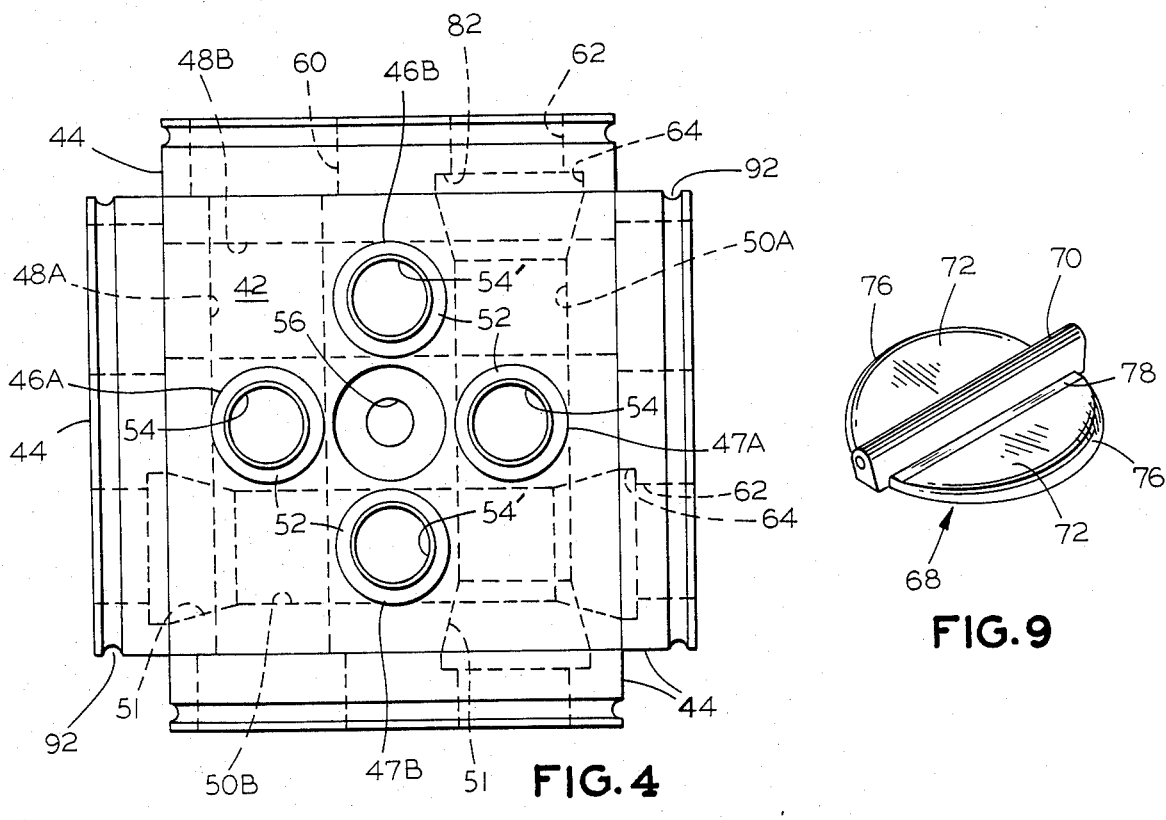
FIG. 4
FIG. 9

HEART PUMP

BACKGROUND OF THE INVENTION

Efforts to develop cardiac prostheses and support devices have been ongoing for many years, with notable success in certain respects. Such activities can generally be categorized as directed either to the provision of an implantable replacement heart, or of an external unit for temporary bypass of, or assistance to, the natural organ. Although the present invention appertains to a heart pump that is intended primarily to serve the latter functions, the concepts involved may indeed have more universal applicability.

It has, in any event, been recognized in the art that the manner in which such an artificial pump effects blood flow is of crucial importance to its feasibility, simulating as closely as possible the operation of the corporeal heart. Thus, the unit must be so designed as to permit continuous, uninterrupted inflow, under the influence of virtually no negative pressure. These conditions avoid the imposition of unnatural loads upon the vascular system of the subject, and permit an inherent balance to be established between the systemic and pulmonary circuits. Moreover, the discharge from the pump must be of a pulsitile nature, to ensure effective dispersion of the blood throughout all vessels of the body.

The foregoing principles have been enunciated in U.S. Pat. No. 3,518,033 to Andersen, who discloses an extracorporeal heart which consists essentially of lengths of normally flat rubber tubing associated with a valve structure. The arrangement is such that an artificial atrium and ventricle chamber are defined in adjacent portions of the tubing, by sequential operation of two valve structures. While the Andersen device endeavors to incorporate principles that are necessary to the provision of a successful mechanical heart pump, it nevertheless suffers from serious deficiencies. In particular, to ensure utmost effectiveness and reliability, it is highly desirable that a unit of this sort be as simple as possible, whereas the two-chamber arrangement and the drive and valving system utilized by Andersen is quite complex. Moreover, such a device would require relatively high levels of operating force, and the simultaneous actuation of both halves of the system (simulating the two sides of the heart), as taught by Andersen, are similarly undesirable. While the art proposes a wide variety of cardiac devices, some of which may avoid certain deficiencies that can be identified in the Andersen unit, it is not believed that there has heretofore been proposed a heart pump having those features which are optimal for utmost effectiveness and feasiblity.

Accordingly, it is a primary object of the present invention to provide a mechanical heart pump which is simple and reliable, and which operates with a continuous, uninterrupted and non-sucking inflow characteristic, and a pulsatile discharge of the blood.

It is also an object of the invention to provide such a novel pump which is comprised of relatively few parts which are themselves of uncomplicated design, and in which the characteristics of the pumping cycle can readily be altered.

Another object of the invention is to provide a pump having the foregoing features and advantages, in which the constant availability of inflow capacity is insured, and in which the flow passage length and pumping volume are minimized.

Yet another object of the invention is to provide such a pump which is relatively easy to install and disconnect from the subject during surgical procedures.

SUMMARY OF THE INVENTION

It has now been found that certain of the foregoing and related objects of the invention are readily attained in a mechanical cardiac pump comprised of a body having a pair of passages extending therethrough with their opposite ends opening at first and second spaced locations thereon. A plurality of passively distensible bladders or sacs are engaged upon the body about each of the spaced locations to sealingly enclose, and provide communication between, the corresponding ends of the passages. Adjacent each of the opposite ends of the passages is provided a check valve, the valves being such as to permit only outflow from one of the passages and only inflow to the other one thereof. Means is provided for independently connecting the passages, intermediate the opposite ends thereof, to the vascular system of the subject. As a result, blood from the subject is capable of flowing naturally into the sacs and can be discharged therefrom by the application of compressive force thereupon.

Generally, the first and second locations at which the opposite ends of the passages open will be disposed on opposite sides of the body of the pump. A second pair of such outflow and inflow passages will preferably be provided through the body, the opposite ends thereof opening at third and fourth spaced locations and being connectable by connecting means in the manner described above. A passively distensible bladder will be engaged about each of the third and fourth spaced locations to establish comparable communication. Consequently, the first-mentioned and second pairs of passages through the body, with their associated bladders, will comprise first and second subsystems of the pump, respectively, adapted to simulate the functions of the two sides of the human heart Normally, in the above-described embodiment, the first and second locations will be on opposite sides of the body, and the third and fourth locations will be similarly disposed with respect to one another and aligned on an axis that is perpendicular to the axis between the first and second locations. As will be appreciated, in such a case the pump body will suitably be of a generally cubic configuration, with the several locations being disposed on each of the four sides thereof. The body may most advantageously comprise an asembly of a generally cubic block with a circular mounting plate on each of the sides, and most desirably the pairs of passages will be disposed at different levels within the body; in that instance, the connecting means will conveniently comprise a separate channel extending inwardly from the top of the body to each of the passages.

Operation of the pump will normally be achieved with a pumping mechanism disposed adjacent the pump body, and comprising means for periodically exerting compressive force upon each of the bladders. More specifically, the mechanism will generally include a plurality of pistons, each being operatively associated with one of the bladders to effect the compression thereof. Most desirably, the mechanism will include a cam member operatively connected to the pistons, configured to actuate them in timed sequence and to produce predetermined pumping cycle characteristics. The pistons will usually be axially aligned with the bladders on opposite sides of the body, and mounted for axial (or radial, when the pistons are disposed in a circular array about the pump body) reciprocation with respect thereto. In such instances, the cam member will suitably comprise a ring-like structure mounted for rotation about the pistons, and having a cam surface defined thereon through which the necessary operative connections are effected.

Mechanical drive means will normally be provided for the cam member as part of an operating system, which means will advantageously comprise a variable speed electric motor. In certain embodiments, it may be desirable to utilize drive means that is electrically adapted to receive and utilize an electrocardiograph signal to control its speed. This arrangement will enable operation of the pump in synchronization with the heartbeat of the subject, thereby rendering the pump most effective as a cardiac assist unit.

Normally, the passages through the pump body will be of generally circular cross-section. In accordance with a particularly preferred embodiment of the invention, the check valves utilized therewith will comprise generally disk-shaped, bileaflet members of substantially the same diameter as the passages, with each member in turn comprising two semi-circular elements of a resiliently deformable material, and a rigid rib extending diametrically therebetween. Each semi-circular element or leaf of the valve member will have a substantially flat rear surface and will taper from a relatively thick and non-deformable section, at a point most remote from the rib, to a line of relatively thin section thereadjacent, thereby providing an integral hinge along the rib about which the element can flex. To adapt the pump for use with such check valves, the body will be provided with suitably directed abutment shoulders adjacent the opposite ends of the passages, so that the valve members can be mounted therein with their flat rear surfaces normally disposed substantially against the shoulders. Consequently, the valves will permit flow from the rear, and will prevent flow in the opposite direction through the associated passage.

BRIEF DESCRIPTION OF THE DRAWINGS

FIG. 3 is an elevational view of the heart pump assembly utilized in the system of the foregoing figures, in partial section and showing one of the cup-shaped sacs mounted in place thereon and a second displaced therefrom;

FIG. 4 is a plan view of the pump body subassembly, drawn to an enlarged scale and illustrating the flow passages provided therein;

FIG. 9 is a perspective view of one of the bileaflet check valve members utilized in the pump, drawn to a greatly enlarged scale.

DETAILED DESCRIPTION OF THE ILLUSTRATED EMBODIMENT

Figure 1:
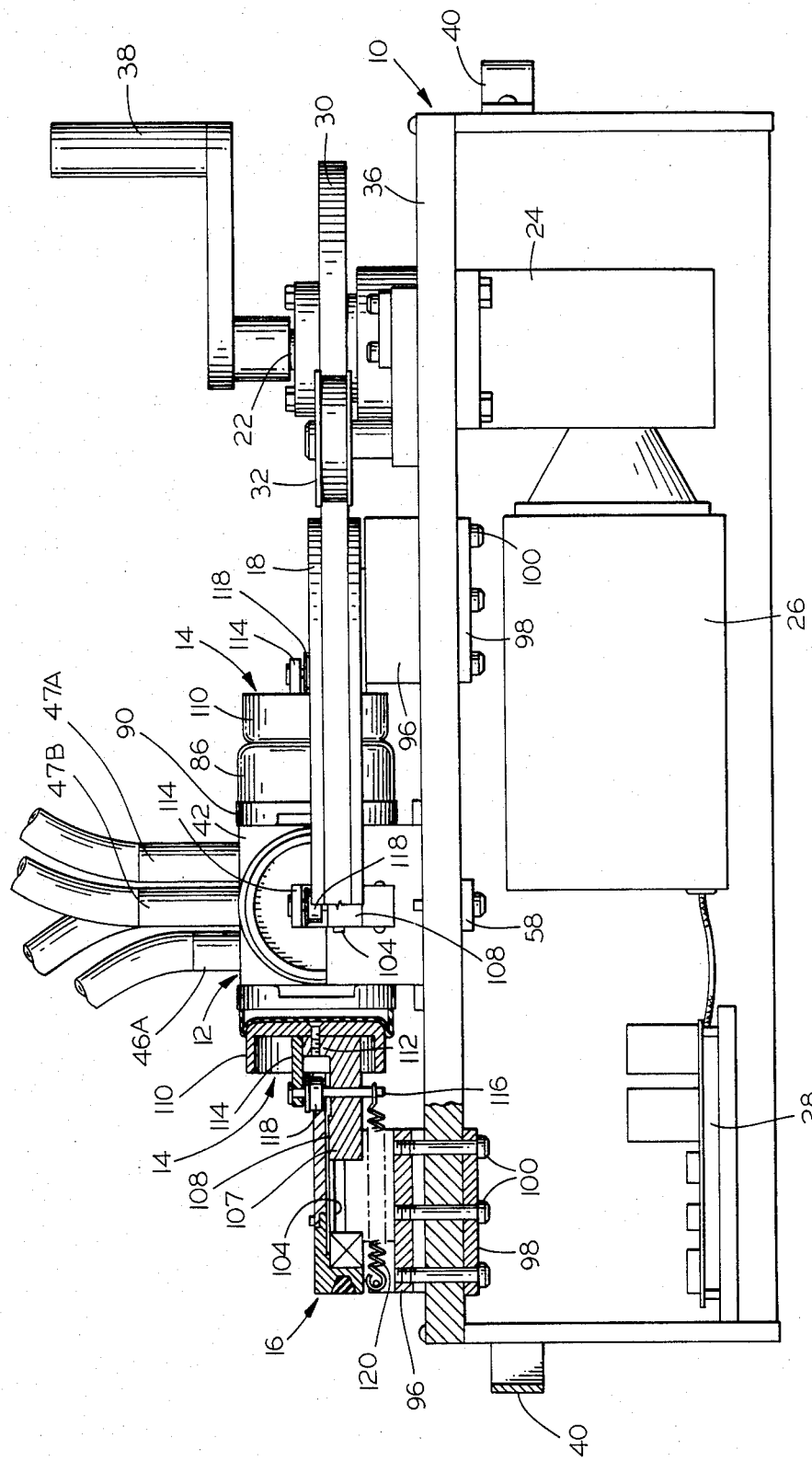
FIG. 1 is a side elevational view, in partial section, of a heart pump system embodying the present invention.
Figure 2:
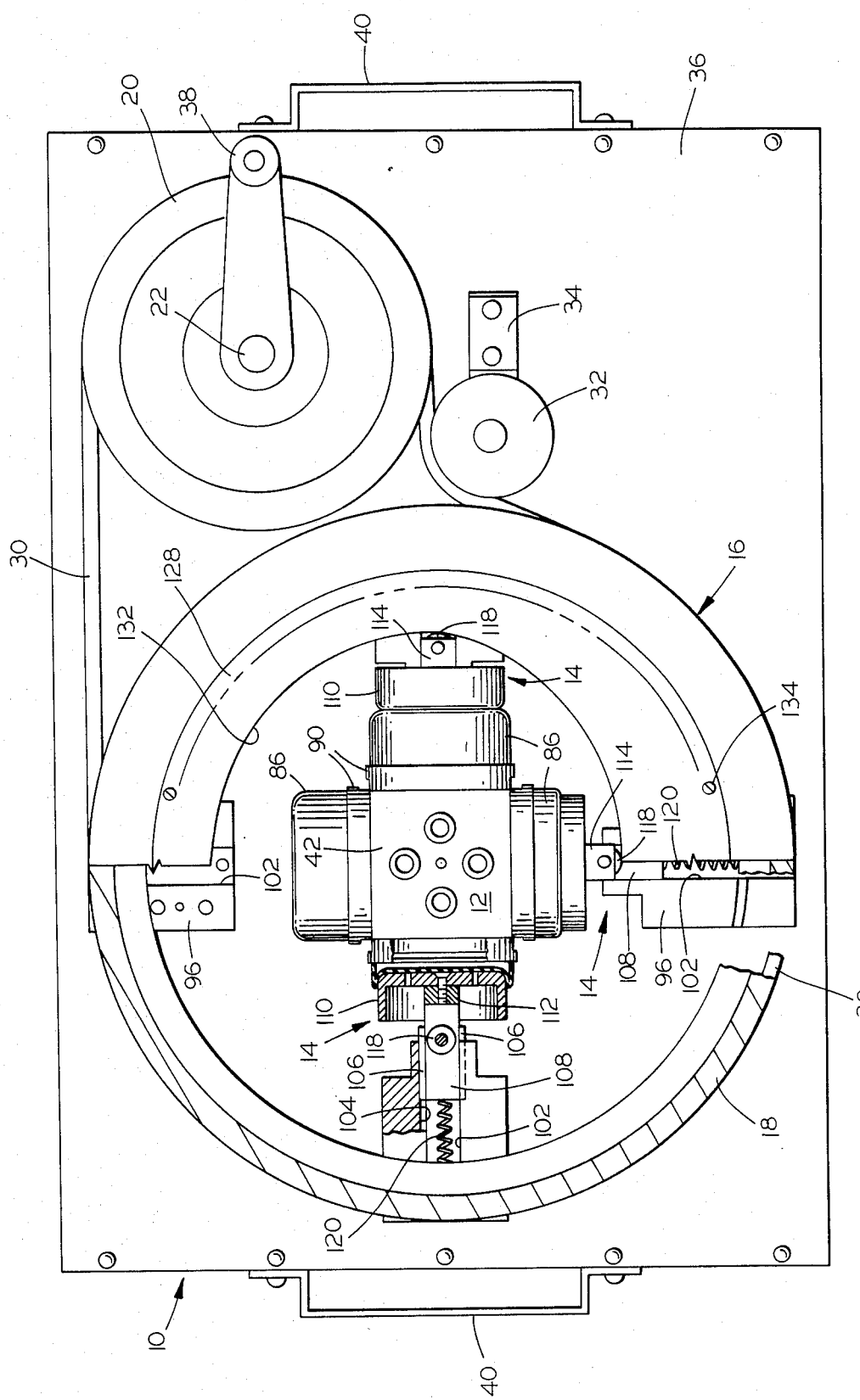
FIG. 2 is a plan view of the system of FIG. 1, also shown in partial section.

Turning initially to FIGS. 1 and 2 of the drawings, therein illustrated is a heart pump system embodying the present invention. The system consists of a frame base, generally designated by the numeral 10, on the top panel 36 of which is mounted, in a central position, a pump assembly, generally designated by the numeral 12. Four piston assemblies, each generally designated by the numeral 14, are mounted on the panel 36 at equidistantly spaced, circumferential locations about the pump assembly 12, it being noted that the operating piston itself is removed at one of the locations shown in FIG. 2, for clarity of illustration. Disposed about the pump and piston assemblies is a cam assembly, generally designated by the numeral 16, having a sheave 18 in operative connection to a pulley 20, which is, in turn, mounted upon the shaft 22 of a gear box unit 24. The latter is driven by a variable speed electric motor 26 which is, in turn, controlled by an direct current power supply unit 28. Connection between the sheave 18 and the pulley 20 is achieved with a V-belt 30, which passes partially about a tension-adjusting idler wheel 32, supporting upon an appropriate mount 34. A removable hand crank 38 is mounted upon the shaft 22 of the pulley 20, and is utilized for manual operation of the system through a one-way clutch arrangement (not shown) as will be discussed subsequently. Handles 40 are attached to the opposite ends of the base 10 to facilitate carrying, contributing to the high portability of the system.

Figure 5:
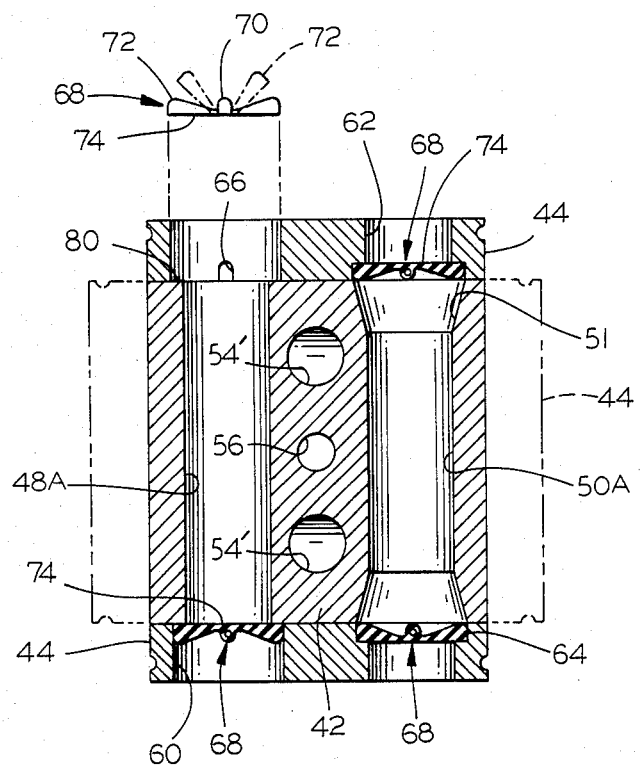
FIG. 5 is a sectional view of the pump body subassembly, taken generally through the plane of the upper level passages, but showing the orientation of the check valves in the mounting plates altered for clarity of illustration, one of the valve members being removed and shown in flexed position in phantom line, as are shown two of the bladder mounting plates.

Turning now in greater detail to FIGS. 3–5, the pump assembly 12 consists of a sub-assembly, which includes a generally cubical block body 42, four disc-shaped mounting plates 44, and four upstanding connecting pipes 46A, 46B, 47A and 47B. The body 42 has two pairs of parallel passages extending therethrough, one pair (48A, 50A) being disposed in the upper part of the body, and the other pair (48B, 50B) being disposed at a level therebelow and in a perpedicular orientation thereto. As can be seen, the passages 48A, 48B are of uniform circular cross-section throughout their length, whereas passages 50A, 50B have flared ends for reasons to be discussed. Upper level passages 48A, 50A are connected through bores 54 to pipes 46A, 47A respectively, and lower level passages 48B, 50B are similarly connected to pipes 46B, 47B. As will be noted, each of the upstanding pipes has a barbed nipple portion 52 thereon to securely engage within the end of the tubing which is utilized to connect the patient to the system, the pipes 46,47 being of different lengths to facilitate the installation of the device by enabling ready differentiation between the inflow (i.e., the shorter pipes 46A, 46B) and the outflow (i.e., the longer ones 47A, 47B) effects from the pump, as will also be more fully discussed below. Disposed centrally of the bores 54 is an axial bore 56 that extends entirely through the block 42, to receive the threaded fastener 58 by which it is mounted upon the top plate 36 of the frame base 10 (see FIG. 1).

Each of the disc-shaped end mounting plates 44 has a pair of apertures formed therethrough, one of which (60) is of uniform circular cross-section, and the other of which consists of a relatively small diameter outer portion 62 and a relatively large diameter inner portion 64. A pair of slots 66 (one of which is visible in FIG. 5) are formed, at diametrically spaced locations, into the surfaces defining both apertures in each plate 44 (although visable in only one instance), the slots 66 extending a short distance outwardly from the inner faces thereof. As best seen in FIG. 9, the bileaflet valve members, generally designated by the numeral 68, have diametrical rib portions 70, which extend beyond the margins of the main, disc-shaped body and provide end portions for engagement in the slots 66, thereby enabling mounting of the valve members 68 within the plates 44 against the body 42. The semi-circular elements 72 of the valve member 68 have substantially flat rear surfaces 74, and taper from a relatively thick and non-deformable section 76 (at a point most remote from the rib 72) to a line of relatively thin section 78 thereadjacent. This provides an integral hinge along the rib 70 about which the semi-circular elements 72 can flex.

As best seen in FIG. 5, one of the valve members 68 is manually mounted against the block body 42 at each of the opposite ends of the passage 48A with the rear surfaces 74 disposed upon the annular shoulder or seat 80, which is defined at the intersection of the passage 48 with the apertures 60 in the two end plates 44 affixed on the body 42 at the opposite ends thereof. As a result, the valve elements 72 are free to flex outwardly (relative to the passageway 48) but not inwardly, thereby functioning as a check valve to permit flow from the passageway 48, but not thereinto. The other passageway 50A has valve members 68 of the same construction mounted at its opposite ends, but with a reverse orientation so as to permit inward, but not outward, flow. The sections 62, 64 of the compound apertures define an annular seats 82 therebetween, against which the valve members 68 are installed, it being noted that the flared sections 51 at the ends of the passage 50 provide the clearance necessary to permit inward opening movement of the valve elements. The taper also defines a gradual transition section and thereby minimizes fluid shear, which could otherwise degrade the blood flowing into the passage from the sacs 86, in view of the relatively high flow velocities that are produced. It should be appreciated that, although the valve members are shown to be in close surface contact against the underlying shoulders, such a condition need exist only when flow past the valve is to be prevented; a slightly open condition at rest is entirely satisfactory and may, indeed, normally be the case.

The circular mounting plates 44 are secured to the block body 42 by appropriate means, such as threaded fasteners 84, as shown in FIG. 3. Although not illustrated, suitable gasket material would normally be interposed between the mating faces of the mounting plates 44 and the pump body 42; however, gaskets can be dispensed with at these locations if the plates are secured by other means, such as adhesive bonding. While permanent securing of the mounting plates to the body would of course preclude replacement of the check valves (should they become ineffective for some reason) one of the outstanding features of the present invention resides in the ability to readily remove and discard the pump sub-assembly (comprising the block body and the attached mounting plates and pipes) after a single use, due to the simplicity and relatively low cost of the sub-assembly. This not only minimizes any concern for durability, but it also obviates any need for cleaning of the device, as would be necessary to permit reuse.

Figure 6:
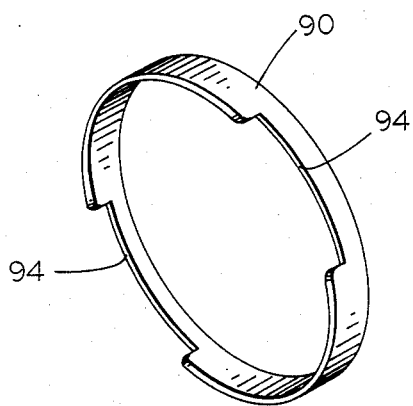
FIG. 6 is a perspective view of the retaining ring utilized cooperatively to secure the bladders on the mounting plates.

The bladders or sacs 86 are fabricated from a supple and relatively flaccid rubbery material, so as to render them passively distensible. In other words, the sacs exhibit no significant tendency to return from a compressed to an extended condition, due to any inherent elasticity or other quality. They are, moreover, sufficiently flaccid to enable fillage with blood to occur with virtually no pressure being required to distend the sac. As best seen in FIG. 3, to effect mounting, the bladder 86 is first inserted over the plate 44, following which an O-ring 88 is stretched over it and is seated in the circumferential groove 92 formed in the circumferential edge of the plate 44. Then the continuous, ring-shaped aluminum clamp 90 is placed over the plate 44 to ensure that the O-ring 88 will remain engaged within the groove 92, thus providing a high degree of assurance against leakage from the bladder. As can be seen in FIG. 6, the ring clamp 90 is narrowed at two locations 94 which are diametrically disposed thereon; this is done to provide the clearances necessary to permit placement of the adjacent clamps, in flush positions against the respective faces of the body 42, without interference.

Referring again in particular to FIGS. 1 and 2, each piston assembly 14 consists of a bearing mount or block 96, fabricated from a metal such as bronze or the like, affixed to the top plate 36 of the base frame 10 by a cleat 98 and bolts 100. The block 96 has a channel 102 extending through it which, in turn, has an elongated groove 104 formed in each of its inner sidewall surfaces, to engage the tongue portions 106 that extend longitudinally along the opposite sides of the base 107 of the slider, generally designated by the numeral 108, which is thereby slideably mounted in the block 96. The slider 108 has a piston head 110 secured to its forward leg 112 by a threaded fastener (unnumbered), and an arm 114 extends rearwardly from upper edge of the leg 112 and the piston head 110. A mounting pin 116 is inserted downwardly through a hole in the free end of the arm 114, and through an aligned bore in the slider base 107; it mounts a cam wheel 118 below the arm 114, and has one end of a coil spring 120 attached to its lower end. The opposite end of the coil spring is secured to a transverse pin (unnumbered) affixed to the bearing block 96; as will be appreciated, therefore, the slider 108, and hence the piston head 110, will be biased in a radially outward direction, away from the pump assembly 12.

Figure 7:
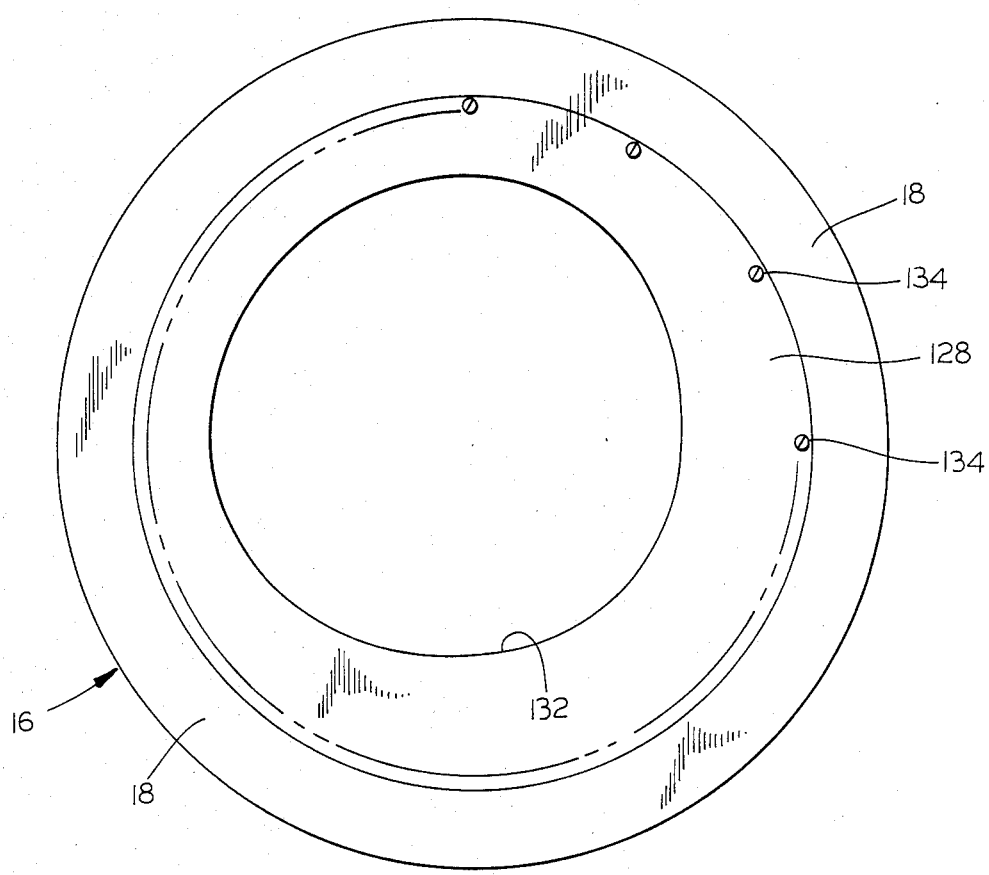
FIG. 7 is a plan view of the cam assembly utilized in the pumping system.
Figure 8:
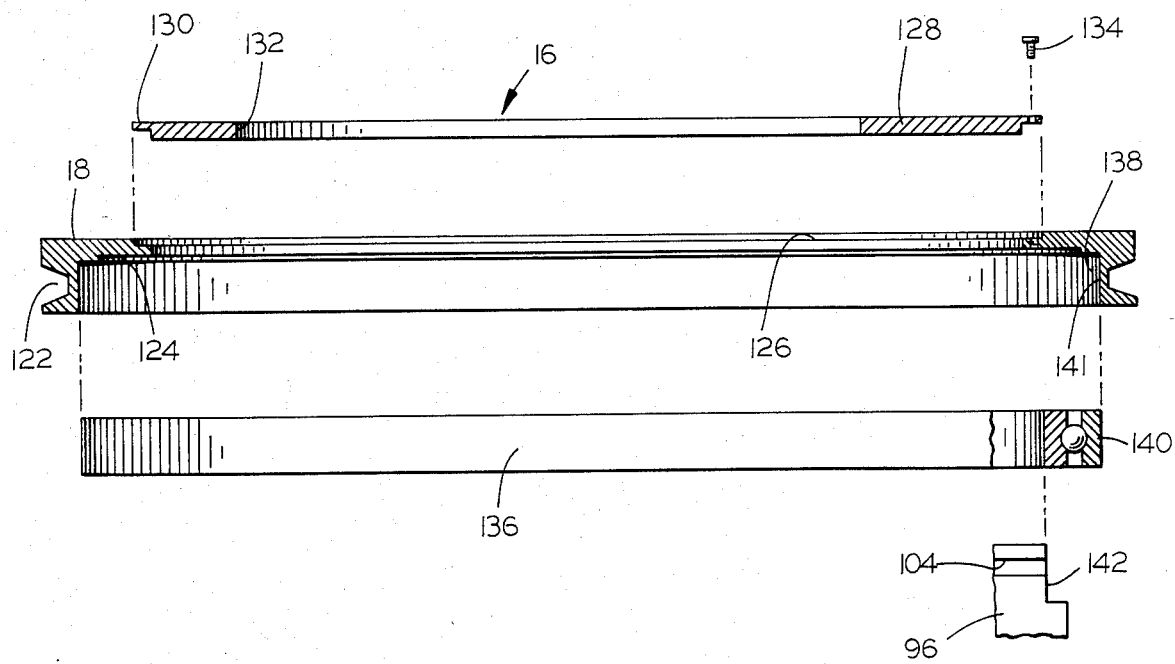
FIG. 8 is an exploded elevational view of the cam assembly, shown in partial section and fragmentarily illustrating a cooperating portion of the bearing block upon which it is supported.

Turning now to FIGS. 7 and 8, the cam assembly is described in detail, and consists of a sheave 18 having a generally V-shaped groove 122 formed in its circumferential edge, and an inwardly projecting lip portion 124 with a peripheral recess 126 formed thereabout. The recess 126 is dimensioned and configured to seat a generally annular cam element 128 therein, which has an outside peripheral flange portion 130 configured to seat within the recess 126 in the top surface of the sheave 18. The inside edge of the cam element 128 defines a continuous, generally curvilinear closed cam surface 132, the configuration of which controls the operation of the sliders 108 through contact on the cam wheels 118, and thereby the pumping action of the piston assemblies 14. As will be noted, the cam element 128 is adapted to be affixed to the sheave 18 by threaded fasteners 134, thereby enabling facile replacement to change the characteristics of the pumping cycle and thereby the flow of blood through the unit, if so desired.

A ring bearing 136 is seated within the recess 138 defined under the lip 124 of the sheave 18, and has its outer race 140 in frictional engagement with the vertical wall 141 thereof. The inner race 142 is in frictional engagement with the four bearing mounts 96 of the piston assemblies 14, which mounts are relieved at 142 for that purpose. Consequently, the cam assembly 16 is supported securely on the top plate 36, for free and virtually frictionless rotation of the sheave 18 and, in turn, the cam element 128.

Although the pumping effect achieved with the system illustrated lends itself to a high degree of sophisticated control upon the flow of blood, operation of the device is very simple. Flow into the pump is achieved through a simple siphon effect, and therefore the rate thereof will be a function of gravity and will depend upon the relative position of the unit below the level of the patient. As will be appreciated, current from the power supply 28 drives the motor 26 which, in turn, drives the shaft 22 on which the pulley 20 is engaged, power transmission occurring through the gear box unit 24. Rotation of the pulley 20 drives the sheave 18 through the V-belt 30, which causes the cam element 128 to rotate about the pump assembly 12. Through contact of the cam surface 132 upon the cam wheels 118 attached to each of the sliders 108, the cam element 128 forces the piston heads 118 to move inwardly along their respective linear paths into contact with the bladders 86, thereby compressing them through a stroke cycle that is controlled by the configuration of the cam surface 132. The piston heads 110 in turn compress the bladders 86, thereby expelling the blood contained therein through the associated discharge passage 50A, 50B to which the bladder opens. During normal operation, the crank handle 38 will be removed from the shaft 22; it is provided primarily for use in emergency situations, such as when a power failure prevents operation of the motor 26, and for use during initial setting-up operations. In this regard, a saline solution will normally be pumped through the system before it is connected to the patient, for the purpose of purging any oxygen that might be present and to ensure that the pump is in good operating order, and this will best be done manually.

The nature of blood flow through the pump will also be readily understood, particularly in view of the illustrations of FIGS. 3–5 of the drawings. Blood from the subject flows into the bladders 86 through the constant diameter passages 48A, 48B, the shorter of the pipes 46A, 46B being connected appropriately for that purpose. So long as any bladder is not under compression, blood is free to flow thereinto, past the outwardly opening check valves 68. As the piston head 114 is brought to bear upon its associated bladder 86, any blood contained therein will be expelled past the reversely oriented check valves 68 and into the end-flared passages 50A, 50B. The discharged blood will be forced upwardly through the longer two of the pipes 47A, 47B, for return to the patient (either directly or through an alarm system monitor, or the like) or for passage to an oxygenator when, for example, the system is employed in a pulmonary bypass surgery; the efficiency of oxygenation is enhanced by the pulsatile nature of blood flow thereinto. Withdrawal of the piston heads 110, with consequential relief of pressure upon the sacs 86, is effected by the coil springs 120, with the cam follower wheels 118 being maintained in constant contact against the bearing surface 132 of the element 128, to ensure control throughout the full stroke of the piston.

As indicated above, due to the reciprocating movement of the pistons, the pump of the present invention affords a pulsatile blood out-flow, as opposed to a continuous out-flow of the sort produced by standard roller pumps. Moreover, because the sacs are flaccid and are not connected directly to the piston heads, they passively respond to the natural inflow of blood, and they exert no sucking effect upon the cardiovascular system of the patient. In addition, a system of this nature must of course be sealed against the entry of air, so as to minimize the danger of air embolism, which is a significant problem associated with clinical perfusion techniques now in use. The pump of the invention comprises two closed loops (when properly connected), and thereby also satisfies this criterion. Furthermore, it is so constructed as to enable its output to change automatically to accomodate the demands of the body, thus further reducing the burdens upon the perfusion technician in managing the patient during cardiopulmonary bypass surgery. Because of its closed systems and automatic control, the pump can be used for long term perfusion and cardiac support without the need for constant monitoring by a skilled technician or a computer system, as would otherwise be required.

As also noted above, the present system can be used either during bypass surgery, with the patient's heart dormant, or to synchronously assist a functioning, but faulty or weak, organ. As to the former application, one of the advantages of the system is that the rate at which pumping is effected becomes non-critical, as long as it is adequate to avoid exceeding available capacity. Due to the relatively large containment volumes afforded by the four bladders (each of which would typically contain about 100 cubic centimeters), a relatively wide margin of safety in this respect is provided. On the other hand, should it be desirable to utilize the device in a support mode, it is only necessary that suitable interfacing electronics be installed to control operation of the device in response to an electrocardiogram signal from the patient.

Yet another very significant advantage of the present pump design concerns the facility with which the cycle and stroke pattern can be tailored to meet specific needs, or altered as desired. Thus, as noted above the cam element is readily removed from the assembly, should it be desired to replace it with one having a different profile. At the present time, it is believed that a modified sinusoidal cycle of four, equal-length phases for each piston, wherein dwell intervals intervene between the forward and rearward strokes, provides a highly desirable pumping profile. On the other hand, it is entirely possible that through experience and further analysis a more sophisticated profile will be developed for the cam element, which will afford an optimal flow pattern. Should this occur or, indeed, should it be determined that different flow patterns must be used to best accommodate different circumstances, the design of the present system permits the change to be made quickly and with great facility, simply by replacement of one cam element with another.

As has also been indicated above, the pump can be utilized as either a single-effect or a double-effect unit, single-effect operation being achieved merely by establishing connections between the passages on only one level of the pump body, thereby effectively utilizing only two of the bladders. This would be done, for example, during pulmonary bypass surgery, or for ventricular assist purposes. Double-effect operation would, on the other hand, be used where the unit is to temporarily serve all functions of the heart, with all four pipes being appropriately attached to the pulmonary veins, the vena cava, the aorta, and the pulmonary artery, respectively.

The materials suitable for use in constructing the parts of the present system will be evident to those skilled in the art, in light of the foregoing description of the functions to be performed. Obviously, those parts that are to contact the blood directly must enjoy U.S. Food and Drug Administration approval, as well as having the functional properties necessary for efficient and reliable operation. The body block and the circular mounting plates will, of course, be made of a tough and rigid material, whereas the check valve members and the sacs will be of flexible fabrication. Generally, synthetic resinous materials will be preferred for use virtually throughout the pump assembly, the rigid body being made for example, of medical grade acrylic polymers, polycarbonates, polyesters, and the like; the flexible elements may be made of a medical grade of polyester-based polyurethene, such as that which is available from the CPR Division of the Upjohn Company under the name PELLETHANE CPR 2363-80 A. Typically, the bladder will be about 0.035 inch thick, and molded with a diameter of about 3 inches; the cubical block body will typically measure about 3 inches on a side.

Thus, it can be seen that the present invention provides a novel mechanical cardiac pump that is simple and reliable, and that operates with a continuous, uninterrupted and non-sucking inflow characteristic, and a pulsatile discharge. The pump is comprised of relatively few parts which are, themselves, of uncomplicated design, and which permit the characteristics of the pumping cycle to be readily altered. The pump unit affords the constant availablility of substantial inflow capacity, while minimizing flow passage length and pumping volume, by virtue of the centralized position of the pump assembly within a circular array of piston actuators. The pump is, moreover, relatively easy to install and disconnect from the subject during surgical procedures, and it is relatively low in cost, thus making one-time use practical from an economic standpoint.

Having thus described the invention, what is claimed is:

1. A mechanical heart pump comprising: a body portion having an inlet thereinto and an outlet therefrom; a first conduit connected to said body portion for directing blood from a patient to said inlet; a second conduit connected to said body portion for directing blood from said outlet to a patient; said body portion having a first and a second passage defined therethrough in generally parallel spaced independent relationship to each other, said first passage being disposed in communicative relationship with said inlet and said second passage being disposed in communicative relationship with said outlet, each of said passages having a first opening at one end thereof and a second opening at the opposite end thereof, a first passively distensible bladder sealingly secured to said body portion in circumscription about said first openings of said first and second passages a second passively distensible bladder sealingly secured to said body portion in circumscription about said second openings in said first and second passages; a plurality of check valves disposed in said passages one each adjacent each one of said openings and positioned, respectively, to prevent a back flow from said bladder toward said inlet and prevent a back flow from said outlet toward said bladder; force means operatively associated with said body portion, said force means having a driving means, a driven means, and force transmitting means operatively interposed between said driving means and said driven means, said driven means having an eccentric cam connected thereto in rotatable circumscription about said body portion for selectively engaging one of said bladders while disengaging the other of said bladders to provide a continuous flow of blood from said engaged bladder into said output while permitting a continuous flow of blood from said input into said disengaged bladder.

2. A mechanical heart pump according to claim 1 in which said body portion has four substantially identical lateral faces and said bladders are secured to said body portion, one each on each of said lateral faces.

3. A mechanical heart pump according to claim 1 in which said body portion has four substantially identical lateral faces and said bladders are secured to said body portion, one each on opposite ones of said faces.

4. A mechanical heart pump according to claim 1 in which said force means includes a plurality of self-retracting pistons, one associated with each of said bladders, each of said pistons being positioned relative to said cam to selectively accept force therefrom and compress the associated bladder in response thereto.

5. A mechanical heart pump according to claim 4 in which each of said pistons is axially aligned with a different one of said bladders for reciprocation upon said axis of alignment, said piston having a cam follower disposed upon the outward end thereof operatively engaging said cam for movement in response to the rotating eccentricity thereof.

6. A pump according to claim 1 in which each of said passages are of circular cross-section and each of said check valves comprise generally disk-shaped members, each of said disk-shaped members in turn comprising two semi-circular elements of a resiliently deformable material with a rigid rib extending diametrically therebetween, each of said elements having a substantially flat rear surface and tapering from a relatively thick and non-deformable section at a point most remote from said rib to a line of relatively thin section thereadjacent, thereby providing an integral hinge along said rib about which said element can flex, said pump body having suitably directed abutment shoulders adjacent said opposite ends of each of said passages, said member being mounted therein with said flat rear surfaces normally disposed substantially against said shoulders adjacent thereto whereby said valve member will permit flow from therear thereof and will prevent flow through said passage in the opposite direction.

7. The pump of claim 1 wherein said passages are of generally circular cross-section, and wherein said check valves comprise generally disk-shaped members, each of said members in turn comprising two semi-circular elements of a resiliently deformable material with a rigid rib extending diametrically therebetween, each of said elements having a substantially flat rear surface and tapering from a relatively thick and non-deformable section at a point most remote from said rib to a line of relatively thin section thereadjacent, thereby providing an integral hinge along said rib about which said element can flex, said pump body having suitably directed abutment shoulders adjacent said opposite ends of said passages, and said member being mounted therein with said flat rear surfaces normally disposed substantially against said shoulders, whereby said valve member will permit flow from the rear thereof and will prevent flow through said passage in the opposite direction.

8. A mechanical heart pump comprising: a body portion having an inlet thereinto and an outlet therefrom; a first conduit connected to said body portion for directing blood from a patient to said inlet; a second conduit connected to said body portion for directing blood from said outlet to a patient; said body portion having a first and a second passage defined therethrough in generally parallel spaced independent relationship to each other, said first passage being disposed in communicative relationship with said inlet and said second passage being disposed in communicative relationship with said outlet, each of said passages having a first opening at one end thereof and a second opening at the opposite end thereof, a first passively distensible bladder sealingly secured to said body portion in circumscription about said first openings of said first and second passages, a second passively distensible bladder sealingly secured to said body portion in circumscription about said second openings in said first and second passages; said body portion further having a third and a fourth passage defined therethrough in generally parallel spaced independent relationship to each other in subposed transverse relationship to said first and second passages, said third passage being disposed in communicative relationship with said inlet and said fourth passage being disposed in communicative relationship with said outlet, each of said passages having a first opening at one end thereof and a second opening at the opposite end thereof, a third passively distensible bladder sealingly secured to said body portion in circumscription about said first openings of said third and fourth passages, a fourth passively distensible bladder sealingly secured to said body portion in circumscription about said second openings in said third and fourth passages, said third and fourth bladders being interposed between said first and second bladders on said body portion; a plurality of check valves disposed in each of said passages, one each adjacent each one of said openings and positioned, respectively, to prevent a backflow from said bladders toward said inlet and prevent a backflow from said outlet toward said bladder; force means operatively associated with said body portion, said force means having driving means, driven means, and force transmitting means operatively interposed between said driving means and said driven means, said driven means having an eccentric cam connected thereto in rotatable circumscription about said body portion for selectively engaging one of said bladders while disengaging the others of said bladders to provide a continuous flow of blood from said engaged bladder into said output while permitting a continuous flow of blood from said input into said disengaged bladders.

9. A mechanical heart pump according to claim 8 in which said body portion has four substantially identical lateral faces and said blades are secured to said body portion, one each on each of said lateral faces.

10. A mechanical heart pump according to claim 8 in which said force means includes a plurality of self-retracting pistons, one associated with each of said bladders, each of said pistons being positioned relative to said cam to selectively accept force therefrom and compress the associated bladder in response thereto.

11. A mechanical heart pump according to claim 10 in which each of said pistons is axially aligned with a different one of said bladders for reciprocation upon said axis of alignment, said piston having a cam follower disposed upon the outward end thereof operatively engaging said cam for movement in response to the rotating eccentricity thereof.

12. A pump according to claim 8 in which each of said passages are of circular cross-section and each of said check valves comprise generally disk-shaped members, each of said disk-shaped members in turn comprising two semi-circular elements of a resiliently deformable material with a rigid rib extending diametrically therebetween, each of said elements having a substantially flat rear surface and tapering from a relatively thick and non-deformable section at a point most remote from said rib to a line of relatively thin section thereadjacent, thereby providing an integral hinge along said rib about which said element can flex, said pump body having suitably directed abutment shoulders adjacent said opposite ends of each of said passages, said member being mounted therein with said flat rear surfaces normally disposed substantially against said shoulders adjacent thereto whereby said valve member will permit flow from the rear thereof and will prevent flow through said passage in the opposite direction.

13. A mechanical heart pump according to claim 8 in which said first pair of passages define a central axis which is perpendicular to the central axis defined by said second pair of passages.

14. A mechanical heart pump according to claim 13 in which said body comprises four sides, a top surface and a bottom surface and one of said bladders is attached to a different one of said sides.

15. The pump of claim 14, wherein said body comprises an assembly of a generally cubical block with a circular mounting plate on each of said four sides thereof.

16. A mechanical heart pump according to claim 8 is which said first pair and said second pair of passages are disposed at different levels within said body, each inflow passage having an independent feeding means and each outflow passage having an independent return means operatively associated therewith.

17. A mechanical heart pump comprising: a body having a first pair of passages passing therethrough in generally parallel spaced relationship to each other and a second pair of passages passing therethrough in generally parallel spaced relationship to each other in subposed relationship to said first pair of passages and extending transversely thereof; each of said passages in each of said pairs of passages having a first and a second opening, said first openings providing an inflow of blood into and said second openings providing an outflow of blood from said corresponding passage; a plurality of passively distensible bladders, one being sealingly secured to said body at each end of each said pair of passages in circumscription thereabout to receive the inflow from said inflow passage and supply the outflow to said outflow passage associated therewith; feeding means operatively connectable to a patient to direct the flow of blood from said patient through said inflow passages to a corresponding bladder; force means operatively associated with said body to selectively engage said bladders and express the blood contained therein into the outflow passage corresponding thereto; and return means operatively connectable to the patient to direct the flow of blood from said outflow passages to said patient.

18. The pump of claim 17 wherein one of said pistons is axially aligned with each of said bladders and is mounted for reciprocation on the axis of alignment, and wherein said cam member comprises a ring-like structure mounted for rotation about said pistons and having a cam surface defined thereon through which said operative connection to said pistons is effected.

* * * * *